US006855848B2

United States Patent
Scherer et al.

(10) Patent No.: US 6,855,848 B2
(45) Date of Patent: Feb. 15, 2005

(54) PROCESS FOR PREPARING BISALLYLBORANES AND NONAROMATIC BORONIC ACIDS

(75) Inventors: Stefan Scherer, Büttelborn (DE); Alexei Kalinin, Kingston (CA); Victor Snieckus, Kingston (CA)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/650,370

(22) Filed: Aug. 28, 2003

(65) Prior Publication Data

US 2004/0039233 A1 Feb. 26, 2004

Related U.S. Application Data

(62) Division of application No. 10/236,749, filed on Sep. 6, 2002, now Pat. No. 6,706,925.

(30) Foreign Application Priority Data

Sep. 7, 2001 (DE) .......................................... 101 43 979

(51) Int. Cl.$^7$ ................................ C07F 5/02; C07F 5/04
(52) U.S. Cl. ................................ 568/1; 568/7; 558/286; 558/298; 549/213
(58) Field of Search ................................ 558/286, 298; 568/1, 7; 549/213

(56) References Cited

U.S. PATENT DOCUMENTS

| | | | | |
|---|---|---|---|---|
| 3,133,951 A | * | 5/1964 | Nutzel et al. ............... | 558/298 |
| 3,206,446 A | * | 9/1965 | Melville ..................... | 525/61 |
| 4,978,794 A | | 12/1990 | Brown ......................... | 568/1 |

OTHER PUBLICATIONS

Bezmenov, A. Ya., et al., "Hydroboration of isoprene and cis– and trans– piperylenes", N.D. Zelinskii Institute of Organic Chemistry, Academy of Sciences, USSR, No. 12, pp. 2111–2120, Dec. 1965.

Mikhailove, B.M., et al., et al., et al., "Cyclic boron compounds formed during hydroboration of 1,3–butadiene", N.D. Zelinskii Institute of Organic Chemistry, Academy of Sciences, USSR, vol. 155, No. 1, pp. 141–144, Mar. 1964.

* cited by examiner

Primary Examiner—Peter O'Sullivan
(74) Attorney, Agent, or Firm—Richard P. Silverman

(57) ABSTRACT

A process for preparing bisallylboranes of the formula (I) by reacting a diene with sodium borohydride in the presence of an oxidant:

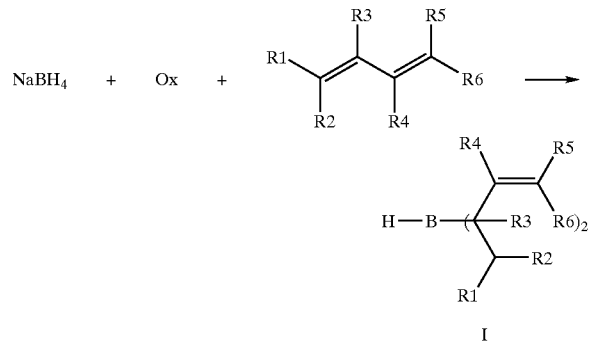

in an inert solvent, with the borane generated in situ reacting selectively with the diene to form the bis(allyl)borane of the formula (I) and the substituents $R^1$ to $R^6$ having the following meanings:

$R^1$ 14 $R^6$ are H, aryl or substituted or unsubstituted $C_1$–$C_4$-alkyl or two radicals R may be closed to form a cyclic system.

As oxidant, it is possible to use, for example, alkyl halides or dialkyl sulfates. In a particularly preferred embodiment, the diene used is 2,5-dimethylhexa-2,4-diene ($R^1$, $R^2$, $R^5$, $R^6$=methyl, $R^3$, $R^4$=H).

3 Claims, No Drawings

PROCESS FOR PREPARING BISALLYLBORANES AND NONAROMATIC BORONIC ACIDS

This application is a Divisional application of application Ser. No. 10/236,749, filed Sep. 6, 2002, now U.S. Pat. No. 6,706,925, the contents of which are hereby incorporated by reference.

Aromatic boronic acids have become indispensible in the synthesis of complex organic molecules. They make it possible to produce many structures which are otherwise obtainable only with difficulty.

Many examples of such Suzuki reactions are reported in the chemical literature. Among these, C—C coupling reactions in which aliphatic or olefinic boronic acids are used are relatively rare.

One reason for this is the usually challenging synthesis of new nonaromatic boronic acids which are of interest for research. Such boronic acids would allow the introduction of interesting substructures which cannot be achieved or achieved only with difficulty by means of classical synthesis.

Aliphatic and olefinic boronic acids are usually prepared by means of hydroboration of alkenes and alkynes or else via conversion of haloolefins into Grignard compounds and addition of the resulting organomagnesium compounds onto esters of boric acid. However, these reactions frequently display only low chemoselectivities and regioselectivities. Examples are the reaction of catecholborane with styrenes or the reaction of alkylmagnesium halides with boric esters.

The handling of boranes on an industrial scale, in particular, is often an obstacle because of their hazardous properties.

The present invention describes a simple, direct route to alkylboronic and alkenylboronic acids via the corresponding bis(allyl)boranes which gives good yields and can be carried out in a single vessel.

The present invention accordingly provides a process for preparing bis(allyl)boranes of the formula (I) by reacting a diene with sodium borohydride in the presence of an oxidant in an inert solvent, with the borane generated in situ reacting selectively with the diene to form the bis(allyl)borane of the formula (I). The first step of the reaction generates borane which dimerizes in the absence of the diene to form diborane but reacts with the diene to form the corresponding bis(allyl) borane highly selectively.

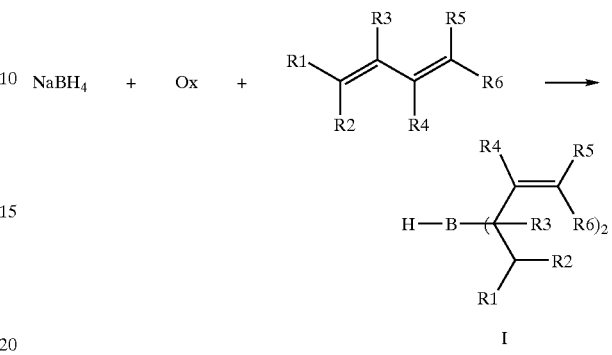

This route to bis(allyl)boranes is novel and was thus not to be expected since the reaction of borane with dienes is described in the literature as largely unselective, giving predominantly borolanes as main products (Dokl. Akad. Nauk. SSSR, Ser. Khim. 1964, 155, 141; Izv. Akad. Nauk. SSSR, Ser. Khim. 1965, 2111). Bis(allyl)boranes have hitherto been prepared in the literature via thermal disproportionation reactions.

In a preferred embodiment; the diene used is 2,5-dimethylhexa-2,4-diene ($R^1$, $R^2$, $R^5$, $R^6$=methyl, $R^3$, $R^4$=H).

The alkene or alkyne is added to the bis(allyl)borane which has been generated in this way and is reacted therewith. This reaction proceeds highly regioselectively and chemoselectively. The alkylbis(allyl)borane (V) or alkenylbis(allyl)borane (III) is selectively oxidized in the same vessel to the corresponding bisallyl boronate. The bis(allyl) ester can be isolated as such or converted into a derivative.

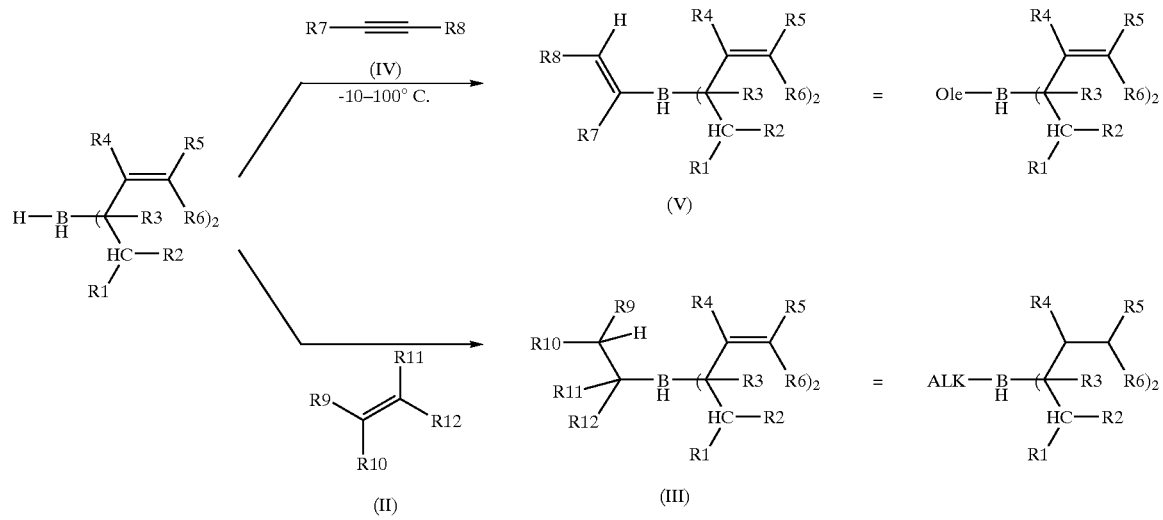

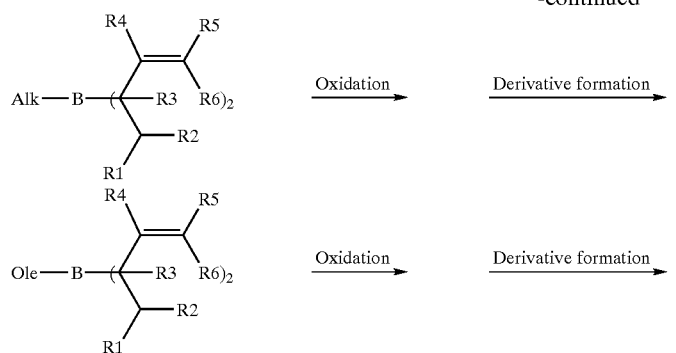

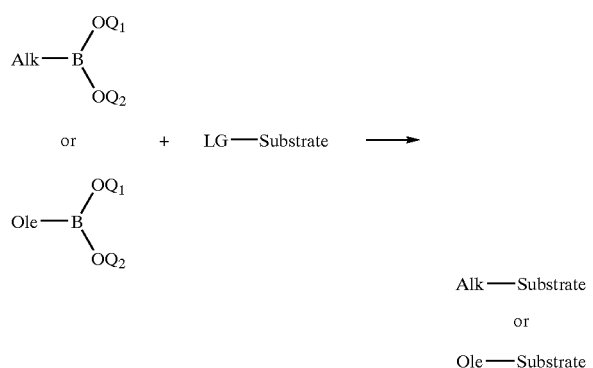

The bis(allyl)boranes and bis(allyl) esters produced can be used in the same vessel in C—C coupling reactions, for example Suzuki reactions. Isolation of the boronic acid can be circumvented. This is particularly useful when the boronic acid is very sensitive to oxidation, heat or hydrolysis.

In the first reaction step, diborane is generated in situ from sodium borohydride by reaction with an oxidant (Ox), e.g. with substituted or unsubstituted $C_1$–$C_8$—, in particular $C_1$–$C_4$-alkyl halides or dialkyl sulfates, preferably with alkyl iodides or bromides or dialkyl sulfates, particularly preferably with dimethyl sulfate, diethyl sulfate, benzyl bromide or iodoethane, in an inert solvent at temperatures of from −20 to +30 ° C., preferably from −5 to +10° C., and this then reacts selectively with the diene present in the reaction mixture to form the corresponding bis(allyl)borane I.

Suitable solvents are, for example, various ethers or hydrocarbons, in particular $C_1$–$C_{10}$ hydrocarbons or mixtures thereof, preferably ethers such as end-proteceted oligoglycol or polyglycol ethers or THF, particularly preferably diglyme, which are inert toward the reactants.

The radicals $R^1$–$R^6$ are H, aryl or $C_1$–$C_4$-alkyl, substituted or unsubstituted, and may be closed to form a cyclic system, e.g. via the radicals $R^1$ and $R^5$ to form a six-membered ring, preferably H and methyl. In a particularly preferred embodiment, 2,5-dimethylhexa-2,4-diene ($R^1$, $R^2$, $R^5$, $R^6$=methyl, $R^3$, $R^4$=H) are employed. The diene is used in an amount of from 1 to 10 molar equivalents based on sodium borohydride, preferably 2–3 molar equivalents. The concentration of the bis(allyl)borane formed is from 0.1 to 5 mol/l, preferably from 0.5 to 2 mol/l.

The present invention further provides a process for preparing boronic acids by reaction of a diene with sodium borohydride in the presence of an oxidant to form the corresponding bis(allyl)borane of the formula (I) and further reaction of the borane (I) with an appropriate alkene (II) or alkyne (IV) to give the alkylbis(allyl)borane (III) or alkenylbis(allyl)borane (V) which is oxidized directly in the presence of an oxidant to form the corresponding bisallyl alkylboronate or alkenylboronate and, if desired, subsequent conversion into a derivative.

The bis(allyl)borane (I) produced in this way is reacted in the same vessel with a substituted alkene (II) or alkyne (IV) at temperatures in the range from −10 to 100° C., preferably from 0 to 50° C., particularly preferably from 0 to 25° C., to form the alkylbis(allyl)borane (III) or alkenylbis(allyl)borane (V), which can advantageously be employed in C—C coupling reactions, in particular in Suzuki coupling reactions.

The radicals $R^7$ to $R^{12}$ are, in particular, aryl, substituted or unsubstituted, ailkyl-($C_1$–$C_8$), which may be branched and/or substituted, alkoxy-($C_1$–$C_8$), acyloxy-($C_1$–$C_8$), O-phenyl, fluorine, chlorine. $NO_2$, $NH_2$, NHalkyl-($C_1$–$C_8$), Nalkyl$_2$-($C_1$–$C_8$), CN, CHO, $SO_3H$, $SO_3R$, $SO_2NH_2$, $SO_2N$(alkyl-($C_1$–$C_8$))$_2$, $SO_2$-alkyl-(C1–$C_8$), COO-alkyl-($C_1$–$C_8$), $CONH_2$, CO-alkyl-($C_1$–$C_8$), NHCHO, $CF_3$, 5-membered heteroaryl or 6-membered heteroaryl. Two radicals can also form a cyclic system which may contain heteroatoms.

The range of alkenes and alkynes which can be used is very wide. The examples given for substituents are only an illustrative selection from the possible range and do not restrict the process of the invention to these.

To avoid selectivity problems in the oxidation, for example in the oxidation of bis(cyclohexyl)boranes to bis (cyclohexyloxy)boronic acids by means of N-oxides as described in the literature (Synthesis, 1988, 103), keto compounds are used according to the invention for the oxidation in the third reaction step after the hydrolysis. It is possible to use, for example, formaldehyde, acetone, glyoxal, diacetyl, preferably formaldehyde and diacetyl.

The oxidation takes place at temperatures of from 0 to 100° C., preferably from 10 to 40° C. The keto compounds are added in a molar ratio of 1–2 based on sodium borohydride used.

The oxidation of alkenylbis(allyl)boranes (V) by means of formaldehyde gives boronic esters of the formula (VI), while that by means of diacetyl gives esters of the formula (VII).

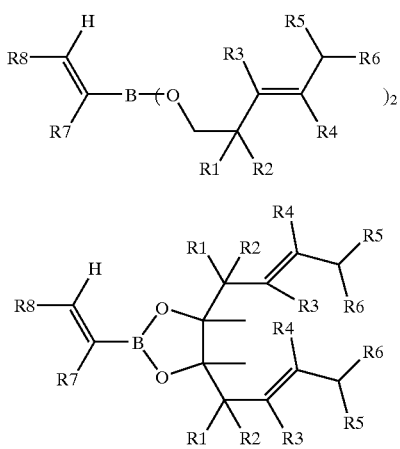

The boronic esters which result from the oxidation of the alkylbis(allyl)boranes (III) have an analogous structure, with the only difference being that the alkyl substituent on the boron is different.

The boronic esters produced in this way can be converted into the appropriate derivatives by known methods. For example, hydrolysis gives the free boronic acids (Q1, Q2=OH), reaction with pinacol gives the corresponding pinacol esters (Q1, Q2=—OC(CH$_3$)$_2$—C(CH$_3$)$_2$O—) and reaction with diethanolamine gives the corresponding diethanolamine esters (Q1, Q2=—OCH$_2$CH$_2$NHCH$_2$CH$_2$O—).

In principle, any desired derivatives can be prepared without problems, for example simple alkyl esters (Q1, Q2=Oalkyl) or cyclic esters derived from ethylene glycol or catecholborane.

The process described offers, in particular, the opportunity of reacting the bis(allyl)boranes (III) and (V) or the ester derivatives (VI) and (VII) (including the corresponding alkylboronic esters from the bis(allyl)boranes (III)) produced in situ with any suitable substrates in a Suzuki coupling. The substrates have to have a leaving group LG, with LG being, in particular, I, Br, Cl or OSO$_2$CF$_3$. Examples of substrates are bromoaromatics or iodoaromatics and also bromoolefins or iodoolefins.

EXAMPLE 1

Preparation of di(1-isopropyl-3-methylbut-2-enyl)borane

NaBH$_4$ (0.757 g, 20 mmol), 2,5-dimethylhexa-2,4-diene (7.10 ml, 50 mmol) and anhydrous diglyme (20 ml) were placed in a baked 100 ml flask under an Ar atmosphere and cooled in an ice bath. (MeO)$_2$SO$_2$ (1.90 ml, 20 mmol) was slowly added while stirring vigorously to the reagent slurry obtained after cooling, with the reaction temperature being kept below 5° C. The addition was accompanied by vigorous gas evolution and clarification of the reaction mixture. The solution formed was stirred at 0° C. for 3 hours, giving a thick suspension of di(1-isopropyl-3-methylbut-2-enyl)borane which was used directly in the hydroboration step.

EXAMPLE 2

General method A

2-[(E)-2-Phenyl-1-ethenyl]-1,3,6,2-dioxazaborocane

Phenylacetylene (2.20 ml, 20 mmol) was added slowly (~20 min) to a suspension of freshly prepared di(1-isopropyl-3-methylbut-2-enyl)borane, with the reaction temperature being below 5° C. The mixture formed was stirred at 0° C. for 1 hour, slowly quenched with H$_2$O (3 ml) (with some gas evolution occurring) and stirred at RT for 0.5 hour, after which a solution of formaldehyde (1.50 ml, 20 mmol, 37% strength by weight solution in water) was added all at once (exothermic reaction, cooling bath necessary). The reaction mixture was stirred at RT for 24 hours and then diluted with EtOAc (40 ml). After separation of the layers, the organic phase was dried briefly (Na$_2$SO$_4$), transferred into a flask with diethanolamine (2.31 g, 22 mmol) and evaporated under reduced pressure (25 mm of Hg, then 0.5 mm of Hg, heating bath 50° C., then 80° C.). The solid residue obtained after evaporation was recrystallized from MeCN, giving the product (3.34 g, 15.38 mmol, 77% yield) in the form of colorless needles, m.p. 194–195° C.; IR (KBr) 3000 br, 1622, 1598, 1573, 1494, 1469, 1454, 1277, 1242, 1206 cm$^{-1}$; $^1$H-NMR (200 MHz, DMSO-d$_6$) 7.38–7.23 (complex, 4H), 7.17–7.14 (m, 1H), 6.84 (br. s, 1H), 6.65 (d, 1H, J=18.1 Hz), 6.23 (d, 1H, J=18.1 Hz), 3.80–3.61 (complex, 4H), 3.08–2.90 (m, 2H), 2.81–2.71 (m, 2H); $^{13}$C-NMR (75.4 MHz, methanol-d$_4$) 140.9, 139.7, 129.6, 129.5, 128.0, 127.3, 64.1, 51.7; MS EI (m/e, relative intensity) (M+ 217).

EXAMPLE 3

2-[(Z)-1,2-Diphenyl-1-ethenyl]-1,3,6,2-dioxazaborocane

This compound was prepared by the general method A from diphenylacetylene (3.56 g, 20 mmol), which was added as a solid to the reaction, and was isolated in a yield of 66% (3.89 g, 13.27 mmol) in the form of colorless crystals, m.p. 227–228.5° C.; IR (KBr) 3222, 3076, 2859, 1595, 1493, 1270, 1198, 1132, 1102, 1070, 1050 cm$^{-1}$; $^1$H-NMR (200 MHz, DMSO-d$_6$) 7.30–6.90 (m, 8H), 6.90–6.80 (m, 2H), 6.71, (s, 1H), 6.58 (br. s, 1H), 3.79–3.65 (m, 2H), 3.65–3.45 (m, 2H), 3.00–2.65 (m, 4H); $^{13}$C-NMR (75.4 MHz, methanol-d$_4$) 146.3, 140.2, 133.9, 130.6, 129.5, 129.4, 128.7, 127.1, 126.3, 63.9, 52.0;

MS EI (m/e, relative intensity) (M+ 293)

EXAMPLE 4

2-[2-(1,1,1-Trimethylsilyl)ethyl]-1,3,6,2-dioxazaborocane

This compound was prepared by the general method A from vinyltrimethylsilane (2.93 ml, 20 mmol) with the reaction mixture being stirred for a further 2 hours at RT before quenching with water and was isolated in a yield of 55% (2.35 g, 10.92 mmol) in the form of colorless needles; m.p. 185–186° C.; IR (KBr) 3090, 2955, 2897, 1461, 1421, 1353, 1296, 1244, 1216, 1159, 1111, 1065, 963 cm$^{-1}$; $^1$H-NMR (200 MHz, DMSO-d$_6$) 6.52 (br. s, 1H), 3.73–3.60 (m, 2H), 3.60–3.50 (m, 2H), 3.05–2.88 (m, 2H), 2.69–2.62 (m, 2H), 0.34–0.20 (m, 2H), 0.20–0.04 (m, 2H), –0.09 (s, 9H); $^{13}$C-NMR (75.4 MHz, methanol-d$_4$) 63.8, 52.2, 11.4, –1.64;

MS EI (m/e, relative intensity) (M+ 215)

EXAMPLE 5

2-(2,3-Dihydro-1H-2-indenyl)-1,3,6,2-dioxazaborocane

This compound was prepared by the general method A from indene (2.33 ml, 20 mmol) with the reaction mixture being stirred for a further 2 hours at RT before quenching with water and was isolated in a yield of 48% (2.24 g, 9.69 mmol) in the form of colorless needles; m.p. 216–219° C. (decomp.); IR (KBr) 3091 br, 2931, 2887, 1482, 1456, 1274, 1244, 1216, 1112, 1067 cm$^{-1}$; $^1$H-NMR (300 MHz, DMSO-d$_6$) 8.28–8.17 (m, 2H), 8.17–8.06 (m, 2H), 7.93 (br. s, 1H), 4.91–4.80 (m, 2H), 4.80–4.70 (m, 2H), 4.45 (d, 1H, J=6.9 Hz), 4.21–4.05 (m, 2H), 3.98–3.82 (m, 4H), 3.76–3.67 (m, 2H); $^{13}$C-NMR (75.4 MHz, methanol-d$_4$) 147.2, 126.4, 124.9, 64.0, 52.3, 36.8;

MS EI (m/e, relative intensity) (M+ 231)

EXAMPLE 6

2-[2-(9H-9-Carbazolyl)ethyl]-1,3,6,2-dioxazaborocane

This compound was prepared by the general method A from N-vinylcarbazole (3.87 g, 20 mmol), which was added as a solid, with the reaction mixture being stirred for a further 8 hours at RT before quenching with water and was isolated using MeOH for the recrystallization in a yield of 67% (4.14 g, 13.43 mmol) in the form of colorless platelets; m.p. 241–244° C. (decomp.); IR (KBr) 3102 br, 1593, 1485, 1452, 1335, 1328, 1272, 1236, 1182, 1104, 1061 cm$^{-1}$; $^1$H-NMR (200 MHz, DMSO-d$_6$) 8.11 (d, 2H, J=7.7 Hz), 7.53 (d, 2H, J=8.1 Hz), 7.42 (td, 2H, J=6.7, 1.0 Hz), 7.14 (td, 2H, J=7.7, 0.7 Hz), 7.00 (br. s, 1H), 4.32–4.19 (m, 2H), 3.85–3.60 (m, 4H), 3.20–3.00 (m, 2H), 2.90–2.70 (m, 2H), 0.85–0.70 (m, 2H); $^{13}$C-NMR (75.4 MHz, methanol-d$_4$) 139.6, 125.3, 121.9, 120.2, 118.0, 109.1, 62.4, 50.7, 40.9;

MS EI (m/e, relative intensity) (M+ 308)

EXAMPLE 7

General Method B:

4,4,5,5-Tetramethyl-2-[(E)-1-octenyl]-1,3,2-dioxaborolane

1-Octyne (2.95 ml, 20 mmol) was added slowly (~20 min) to a suspension of freshly prepared di(1-isopropyl-3-methylbut-2-enyl)borane, with the reaction temperature being below 5° C. The mixture formed was stirred at 0° C. for 1 hour, slowly quenched with H$_2$O (3 ml) (with some gas evolution occurring) and stirred at RT for 0.5 hour, after which a solution of formaldehyde (1.50 ml, 20 mmol, 37% strength by weight solution in water) was added all at once (exothermic reaction, cooling bath necessary). The reaction mixture was stirred at RT for 1 hour and then admixed with pinacol (2.60 g, 22 mmol). After stirring at RT for 24 hours, the mixture was diluted with H$_2$O (40 ml) and extracted with heptane (40 ml), after which the organic extract was washed with H$_2$O (5×25 ml), dried (Na$_2$SO$_4$) and evaporated under reduced pressure. The residue obtained was carefully distilled under reduced pressure (bulb tube), giving 3.19 g of the product (13.39 mmol, 67% yield) in the form of a colorless liquid, b.p. 70–80° C. (0.15 mm of Hg); IR (film) 2928, 1639, 1363, 1319, 1146 cm$^{-1}$; $^1$H-NMR (300 MHz, acetone-d$_6$) 6.55 (dt, 1H, J=18.0, 6.6 Hz), 5.35 (dt, 1H, J=18.0, 1.5 Hz), 2.17–2.09 (m, 2H), 1.50–1.20 (m, 8H), 1.21 (s, 12H), 0.90–0.85 (m, 3H); $^{13}$C-NMR (75.4 MHz, acetone-d$_6$) 155.0, 83.6, 36.5, 32.5, 29.7, 29.2, 25.2, 23.3, 14.4;

MS EI (m/e, relative intensity) (M+ 238).

EXAMPLE 8

4,4,5,5-Tetramethyl-2-[(Z)-1-methyl-2-phenyl-1-ethenyl]-1,3,2-dioxaborolane (Main Component) and 4,4,5,5-tetramethyl-2-[(Z)-1-phenyl-1-propenyl]-1,3,2-dioxaborolane (Secondary Component)

These compounds were prepared by the general method B from 1-phenylprop-1-yne (2.50 ml, 20 mmol) and isolated in a yield of 70% (3.41 g, 13.97 mmol) in the form of a colorless liquid which, according to $^1$H-NMR, was an 83:17 isomer mixture; b.p. 75–90° C. (0.2 mm of Hg); $^1$H-NMR (300 MHz, acetone-d$_6$) 7.42–7.10 (complex, 5H), 7.20 (br. s, 0.83H) and 6.70 (q, 0.17H, J=7.2 Hz), 1.94 (d, 2.49H, J=1.8 Hz) and 1.72 (d, 0.51H, J=7.2 Hz), 1.28 (s, 9.96H) and 1.23 (s, 2.04H); $^{13}$C-NMR (75.4 MHz, acetone-d$_6$, main component (secondary component)) 143.1(143.1), 138.8 (141.0), 130.2(130.0), 129.1(128.6), 128.2(126.7), 84.1 (84.3), 25.3(25.2), 16.2(16.2).

EXAMPLE 9

4,4,5,5-Tetramethyl-2-phenethyl-1,3,2-dioxaborolane

This compound was prepared by the general method B from styrene (2.29 ml, 20 mmol) with the reaction mixture being stirred for a further 2 hours at RT and was isolated in a yield of 71% (3.28 g, 14.13 mmol) in the form of a colorless liquid, b.p. 70–80° C. (0.1 mm of Hg); IR (film) 2979, 1372, 1322, 1145 cm$^{-1}$; $^1$H-NMR (300 MHz, acetone-d$_6$) 7.27–7.15 (m, 4H), 7.15–7.09 (m, 1H), 2.68 (t, 2H, J=8.0 Hz), 1.18 (s, 12H), 1.03 (t, 2H, J=8.0 Hz); $^{13}$C-NMR (75.4 MHz, acetone-d$_6$) 145.4, 129.0, 128.8, 126.3, 83.7, 30.8, 25.2;

MS EI (m/e, relative intensity) (M+ 232)

EXAMPLE 10

2-(3,3-Diethoxypropyl)-4,4,5,5-tetramethyl-1,3,2-dioxaborolane

This compound was prepared by the general method B from acrolein diethyl acetal (3.05 ml, 20 mmol) with the reaction mixture being stirred for a further hours at RT and was isolated in a yield of 63% (3.26 g, 12.63 mmol) in the form of a colorless liquid; b.p. 65–80° C. (0.25 mm of Hg); IR (film) 2977, 2932, 2880, 1371, 1325, 1147, 1127, 1061 cm$^{-1}$; $^1$H-NMR (200 MHz, acetone-d$_6$) 4.39 (t, 1H, J=5.7 Hz), 3.65–3.35 (m, 4H), 1.65–1.55 (m, 2H), 1.20 (s, 12H), 1.12 (t, 6H, J=7.0 Hz), 0.74 (t, 2H, J=8.0 Hz); $^{13}$C-NMR (125.8 MHz, acetone-d$_6$) 104.8, 83.5, 61.4, 28.8, 25.1, 15.7;

MS EI (m/e, relative intensity) (M+ 258)

EXAMPLE 11

4-[2-(4,4,5,5-Tetramethyl-1,3,2-dioxaborolan-2-yl) ethyl]-1,3-dioxolan-2-one

This compound was prepared by the general method B from 4-vinyl-1,3-dioxolan-2-one (1.92 ml, 20 mmol) with the reaction mixture being stirred for a further 2 hours at RT and using EtOAc (80 ml) in the extraction step in a yield of 77% (3.72 g, 15.37 mmol) in the form of a colorless oil; b.p. 105–120° C. (0.25 mm of Hg); IR (film) 2980, 2933, 1805, 1381, 1328, 1166, 1145, 1066 cm$^{-1}$; $^1$H-NMR (300 MHz, acetone-d$_6$) 4.81–4.71 (m, 1H), 4.59 (td, 1H, J=8.1, 0.6 Hz), 4.15 (dd, 1H, J=8.1, 6.9), 1.86–1.76 (m, 2H), 1.22 (s, 12H), 0.85–0.76 (m, 2H); $^{13}$C-NMR (75.4 MHz, acetone-d$_6$) 155.7, 84.0, 79.1, 69.9, 28.9, 25.23, 25.16;

MS EI (m/e, relative intensity) (M+ 242)

EXAMPLE 12

General Method C:

trans4,5-Dimethyl-2-[(E)-2-phenyl-1-ethenyl]-4,5-di [(E)-1,1,4-trimethyl-2-pentenyl]-1,3,2-dioxaborolane Phenylacetylene (2.20 ml, 20 mmol) was added slowly (~20 min) to a suspension of freshly prepared di(1- isopropyl-3-methylbut-2-enyl)borane, with the reaction temperature being kept below 5° C. The mixture formed was stirred at 0° C. for 1 hour, after which 2,3-butanedione (1.93 ml, 22 mmol) was added all at once (exothermic reaction, cooling bath required). After stirring at RT for 12 hours, the reaction mixture was evaporated under reduced pressure, diluted with H$_2$O (40 ml) and extracted with heptane (40 ml). The organic extract was washed with H$_2$O (3×20 ml), dried (Na$_2$SO$_4$) and evaporated, after which the residue obtained was distilled under reduced pressure (bulb tube), giving 6.06 g (14.34 mmol, 72% yield) of the product in the form of a colorless viscous oil; b.p. 140–155° C. (0.1 mm of Hg); IR (film) 2960, 1626, 1578, 1451, 1388, 1352, 1326, 1209, 1082 cm$^{-1}$; $^1$H-NMR (200 MHz, acetone-d$_6$) 7.63–7.58 (m, 2H), 7.45 (d, 1H, J=18.4 Hz), 7.46–7.35 (m, 3H), 6.27 (d, 1H, J=18.4 Hz), 5.71 (dd, 2H, J=15.8, 1.1 Hz), 5.35 (dd, 2H, J=15.8, 6.8 Hz), 2.30–2.15 (m, 2H), 1.53 (s, 6H), 1.12 (s, 6H), 1.11 (s, 6H), 0.94 (d, 6H, J=6.7 Hz), 0.93 (d, 6H, J=6.7 Hz); $^{13}$C-NMR (75.4 MHz, acetone-d$_6$) 150.4, 138.6, 135.8, 134.8, 129.9, 129.6, 128.0, 92.9, 46.6, 32.4, 26.2, 26.1, 22.95, 22.88, 19.4;

MS EI (m/e, relative intensity) (M+ 422)

EXAMPLE 13 trans-2-[(E)-2-(1,1,1-Trimethylsilyl)-1-ethenyl]-4,5-dimethyl-4,5-di[(E)-1,1,4-trimethyl-2-pentenyl]-1,3,2-dioxaborolane This compound was prepared by the general method C from trimethylsilylacetylene (2.83 ml, 20 mmol) and was isolated in a yield of 59% (4.91 g, 11.73 mmol) in the form of a colorless viscous oil, b.p. 120–130° C. (0.3 mm of Hg); IR (film) 2958, 1596, 1465, 1330, 1279, 1248, 1083 cm$^{-1}$; $^1$H-NMR (300 MHz, acetone-d$_6$) 7.15 (d, 1H, J=21.9 Hz), 6.31 (d, 1H, J=21.9 Hz), 5.66 (dd, 2H, J=15.9, 1.2 Hz), 5.33 (dd, 2H, J=15.9, 6.6 Hz), 2.30–2.15 (m, 2H), 1.49 (s, 6H), 1.08 (s, 12H), 0.94 (d, 6H, J=6.9 Hz), 0.93 (d, 6H, J=6.9 Hz), 0.10 (s, 9H); $^{13}$C-NMR (75.4 MHz, acetone-d$_6$) 157.9, 135.7, 134.8, 93.0, 46.5, 32.3, 26.1, 22.90, 22.86, 19.3, –1.6;

MS EI (m/e, relative intensity) (M+ 418)

EXAMPLE 14 trans-2-(2-Isobutoxyethyl)-4,5-dimethyl-4,5-di[(E)-1,1,4-trimethyl-2-pentenyl]-1,3,2-dioxaborolane This compound was prepared by the general method C from isobutyl vinyl ether (2.61 ml, 20 mmol) with the reaction mixture being stirred for a further 2 hours at RT before addition of the 2,3-butanedione and was isolated in a yield of 73% (6.11 g, 14.53 mmol) in the form of a colorless viscous oil; b.p. 120–130° C. (0.2 mm of Hg); IR (film) 2958, 2870, 1466, 1382, 1322, 1107, 1082 cm$^{-1}$; $^1$H-NMR (200 MHz, acetone-d$_6$) 5.68 (dd, 2H, J=15.8, 1.1 Hz), 5.33 (dd, 2H, J=15.8, 6.8 Hz), 3.56 (t, 2H, J=7.5 Hz), 3.15 (dd, 2H, J=6.6, 1.5 Hz), 2.35–2.15 (m, 2H), 1.90–1.75 (m, 1H), 1.46 (s, 6H), 1.19 (t, 2H, J=7.5 Hz), 1.08 (s, 6H), 1.07 (s, 6H), 0.96 (d, 12H, J=6.7 Hz), 0.87 (d, 6H, J=6.6 Hz); $^{13}$C-NMR (125.8 MHz, acetone-d$_6$) 135.3, 134.0, 92.2, 77.6, 67.7, 45.9, 31.8, 28.8, 25.6, 25.5, 22.4, 19.34, 19.32, 18.8;

MS EI (m/e, relative intensity) (M+ 420)

EXAMPLE 15

(E)-2-(6,6-Dimethylbicyclo[3.1.1]hept-2-ylmethyl)-4,5-dimethyl-4,5-bis(1,1,4-trimethylpent-2-enyl)-[1,3,2]dioxaborolane This compound was prepared by the general method C from (1S)-(–)-β-pinene (3.15 ml, 20 mmol) with the reaction mixture being stirred for another 1 hour at RT before addition of the 2,3-butanedione and was isolated in a yield of 72% (6.56 g, 14.37 mmol) in the form of a colorless viscous oil; b.p. 135–150° C. (0.25 mm of Hg); IR (film) 2957, 2904, 2868, 1466, 1374, 1315, 1083 cm$^{-1}$; $^1$H-NMR (300 MHz, acetone-d$_6$) 5.68 (dt, 2H, J=15.9, 1.2 Hz), 5.33 (ddd, 2H, J=15.9, 6.6, 1.5 Hz), 2.40–2.07 (m, 6H), 2.03–1.80 (m, 4H), 1.60–1.45 (m, 1H), 1.45 (s, 6H), 1.92 (s, 3H), 1.08 (s, 15H), 1.05–1.00 (m, 1H), 0.96 (d, 12H, J=6.6 Hz), 0.94–0.85 (m, 1H); $^{13}$C-NMR (75.4 MHz, acetone-d$_6$) 135.90, 135.87, 134.4, 92.5, 49.5, 49.4, 46.4, 46.3, 42.2, 39.5, 38.0, 34.61, 34.58, 32.39, 32.35, 28.8, 27.46, 27.43, 26.44, 26.38, 26.1, 26.0, 25.8, 23.8, 22.94, 22.93, 19.51, 19.50;

MS EI (m/e, relative intensity) (m+ 456)

What is claimed is:

1. A process for preparing boronic acid esters by reaction of a diene with sodium borohydride in the presence of a first oxidant selected from the group consisting of an alkyl halide, a dialkyl sulfate, and mixtures thereof to form the corresponding bis(allyl)borane of the formula (I):

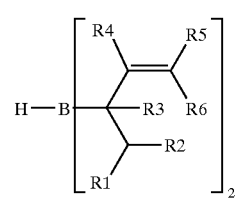

(I)

wherein R$^1$–R$^6$ are H, aryl or substituted or unsubstituted C$_1$–C$_4$-alkyl or two of the radicals R$^1$–R$^6$ may be closed to form a cyclic system, and further reaction of the borane (I) with an alkene (II) or alkyne (IV) to:

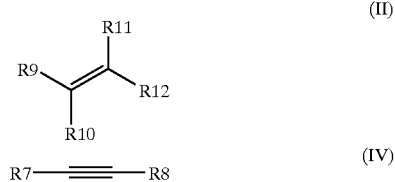

(II)

(IV)

give the alkylbis(allyl)borane (III) or alkenylbis(allyl)borane (V):

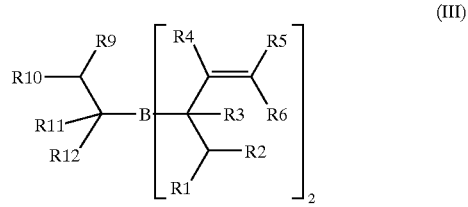

(III)

-continued

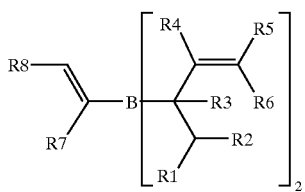

(V)

wherein the radicals $R^7$ to $R^{12}$ are: aryl, substituted or unsubstituted, alkyl-($C_1$–$C_8$), which may be branched and/or substituted, alkoxy-($C_1$–$C_8$), acyloxy-$C_1$–$C_8$), O-phenyl, fluorine, chlorine, $NO_2$, $NH_2$, NHalkyl-($C_1$–$C_8$), Nalkyl$_2$-$C_1$–$C_8$), CN, CHO, $SO_3H$, $SO_3R$, $SO_2NH_2$, $SO_2N(alkyl$-($C_1$–$C_8$))$_2$, $SO_2$-alkyl-($C_1$–$C_8$), COO-alkyl-($C_1$–$C_8$), $CONH_2$, CO-alkyl-($C_1$–$C_8$), NHCHO, $CF_3$, 5-membered heteroaryl or 6-membered heteroaryl, where two or radicals $R^7$ to $R^{12}$ may also form a cyclic ring system which may contain heteroatoms and directly oxidizing the alkylbis(allyl)borane (III) or alkenylbis(allyl)borane (V) In the presence of a second oxidant to form the corresponding bisallyl alkylboronate or alkenylboronate.

2. The process as claimed in claim 1, wherein the second oxidant is selected from the group consisting of formaldehyde, acetone, flyoxal, diacetyl, and mixtures thereof.

3. The process of claim 1, further comprising hydrolyzing the boronic acid esters to form boronic acids.

* * * * *